United States Patent [19]
Andrews et al.

[11] Patent Number: 5,690,684
[45] Date of Patent: Nov. 25, 1997

[54] PIVOT ASSISTED DEFIBRILLATOR PADDLE RETAINER

[75] Inventors: Jonathan N. Andrews, Monmouth; William A. Dixon, Sheridan, both of Oreg.

[73] Assignee: Hewlett-Packard Company, Palo Alto, Calif.

[21] Appl. No.: 432,998

[22] Filed: May 2, 1995

[51] Int. Cl.$^6$ ............................................. A61N 1/39
[52] U.S. Cl. ..................... 607/5; D24/167; D24/168; 248/316.5; 248/222.51
[58] Field of Search ......................... 607/142, 2, 4, 607/5; D24/167, 168; 206/363, 370, 372–375; 248/309.1, 316.4, 222.51, 316.5

[56] References Cited

U.S. PATENT DOCUMENTS

| | | | |
|---|---|---|---|
| D. 252,821 | 9/1979 | Moore et al. | 607/142 |
| D. 288,601 | 3/1987 | MacPherson | D24/168 |
| 1,002,759 | 9/1911 | Rindge | 248/316.4 |
| 3,162,415 | 12/1964 | St. Pierre | 248/316.4 |
| 4,628,935 | 12/1986 | Jones et al. | 607/4 |
| 4,915,109 | 4/1990 | Daynes et al. | 607/2 |
| 5,009,350 | 4/1991 | Schill et al. | 224/324 |
| 5,342,403 | 8/1994 | Powers et al. | 607/5 |
| 5,480,115 | 1/1996 | Haltof | 248/309.1 |

FOREIGN PATENT DOCUMENTS

WO 93/16757  9/1993  WIPO.

*Primary Examiner*—William E. Kamm
*Assistant Examiner*—Carl H. Layno

[57] ABSTRACT

A retainer assembly for a defibrillator paddle has a resilient back plate. The back plate secures to a back wall in a pocket by a fastener positioned to allow pivotal movement of the back plate. The back plate has a bracket at its inner edge, retaining an edge of the base of the paddle. A lip extends forward from an outer edge of the back plate to overlie an outer edge of the paddle. The lip is within a tab section that deflects into a recess if a user exerts a sufficient outward pull on the handle.

17 Claims, 5 Drawing Sheets

PIVOT ASSISTED DEFIBRILLATOR PADDLE RETAINER

FIELD OF THE INVENTION

This invention relates in general to holders for retaining hand-held devices. Particularly, this invention is a retainer for holding a defibrillator paddle.

BACKGROUND OF THE PRIOR ART

A defibrillator is a device for applying an electrical shock to the chest area of a human to initiate heart beat. Defibrillators have electronic circuitry within a housing and two paddles connected by electrical cords. The paddles are retained in pockets on the housing by mechanisms which allow fast and easy withdrawal because the paddles are often used under emergency conditions. Defibrillators may either be mounted to a cart or they may be of a hand carried type.

More specifically, a typical prior art defibrillator paddle pocket has a back wall with a pair of parallel retainer brackets for receiving a portion of the paddle base. A spring engages the base, pressing it against the retainer plates to frictionally hold the paddle in the slot. The paddle is removed by a straight outward pull parallel to the back wall. The spring is sized so that the retention force is not very high, and preferably equal to the force required to withdraw the paddle. In the case of a hand carried defibrillator, the withdrawal force must be less than the weight of the defibrillator to prevent picking up the entire product when the paddles are removed. Keeping the withdrawal force low has forced the retention force to also be low. This prevents the paddles from being securely retained. This is especially a problem in environments where defibrillators have to be hand carried. Paddles which are not securely retained can easily fall out as the defibrillator is jostled during transport.

SUMMARY OF THE INVENTION

A defibrillator paddle retainer assembly has a resilient retainer back plate that is pivotally secured to the back wall of the pocket. A pair of brackets are located on the back plate, defining a slot for receiving an edge of the base of the defibrillator paddle. A lip is also located on the retainer back plate for snapping over an opposite edge of the paddle base to retain the paddle in the slot.

A pull of sufficient force in the withdrawal direction on the handle causes the retainer back plate to resiliently flex. The portion of the retainer containing the brackets moves away from the back wall in one direction while the lip is forced in the opposite direction, rotating about the pivot point. This releases the lip from engagement with the edge of the paddle base, allowing the paddle to be removed. The retainer assembly provides a low withdrawal force and a high retention force for the paddles.

DETAILED DESCRIPTION OF THE INVENTION

Figure 2:
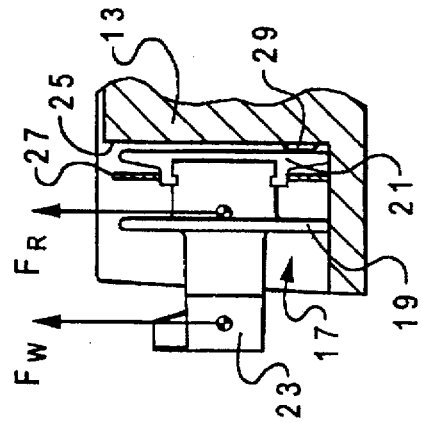
FIG. 2 is a partial sectional view of the defibrillator of FIG. 1 taken along the line 2—2 of FIG. 1.
Figure 1:
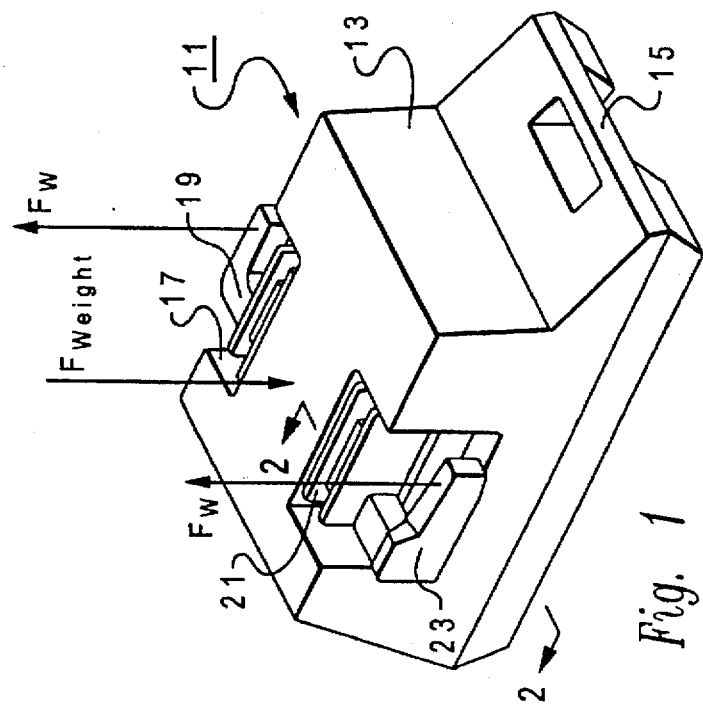
FIG. 1 is a perspective view illustrating a prior art defibrillator.

Referring to FIGS. 1 and 2, a typical prior art defibrillator 11 is shown. Defibrillator 11 is of a hand carried type, having a housing 13 and a handle 15. A pair of pockets 17 are formed on opposite sides of housing 13. A paddle 19 is carried in each pocket 17. Each paddle 19 is a tool which has a flat base 21 and a handle 23 that extends from base 21 perpendicular to the plane of base 21.

Referring to FIG. 2, a back wall 25 of pocket 17 has a pair of stationarily mounted brackets 27 (only one shown) for receiving a portion of paddle base 21. A spring 29 engages base 21 to frictionally hold paddle 19 in the slot formed by brackets 27. FIG. 2 illustrates with arrows a retention force $F_R$ and a withdrawal force $F_W$. For reference only, the direction of $F_W$ and $F_R$, shown upward in the drawing, is considered herein to be "outward", while the opposite or downward direction is "inward". The direction which back wall 25 is facing will be considered the "forward" direction, while the opposite direction will be considered the "rearward" direction.

The friction spring 29 is sized so that the retention force $F_R$ is not very high, and generally equal to the withdrawal force $F_W$. The retention force $F_R$ is the force required to dislodge paddle 19 out of pocket 17 when housing 13 is impacted while being carried, and it acts through the center of mass, as shown. The withdrawal force is the force required to remove paddle 19 during normal use, and it is generated as paddle 19 is lifted straight outward by a user grasping the handle 23. The withdrawal force $F_W$ acts through the centerline of handle 23. The withdrawal force $F_W$ must be less than the weight of the defibrillator 11 to prevent picking up the entire product when the paddles 19 are removed as illustrated by the arrows in FIG. 1. This necessarily has resulted in a low retention force $F_R$, which has the disadvantage of the paddles 19 possibly becoming dislodged while the defibrillator 11 is being carried.

Figure 10:
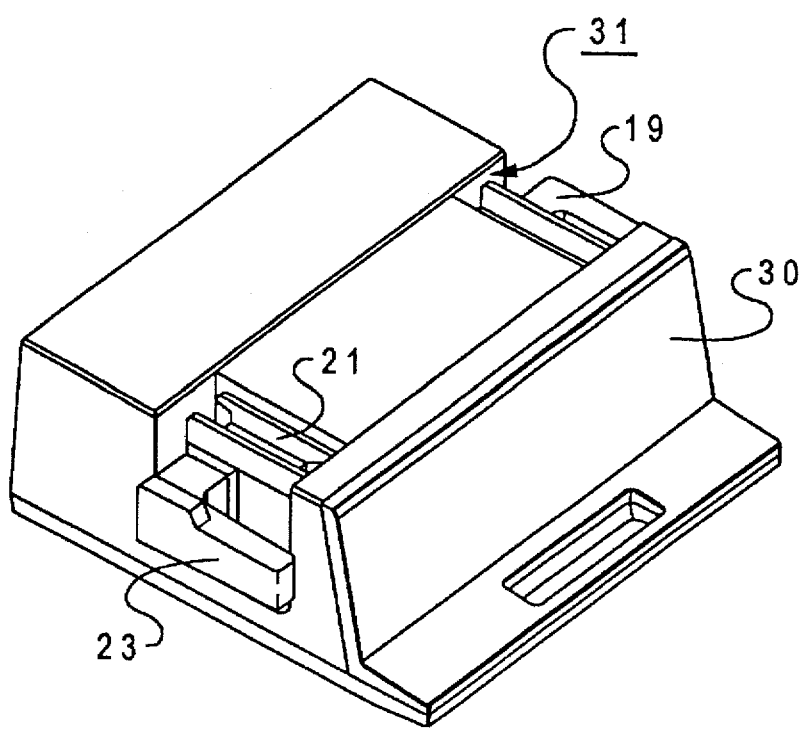
FIG. 10 is a perspective view illustrating a defibrillator having paddle retainer assemblies of the preferred embodiment of the invention.

Referring to FIG. 10, a defibrillator constructed in accordance with this invention is shown. The defibrillator has a housing 30 with a pair of pockets 31 formed on opposite sides of housing 30. The paddles 19 shown are identical to paddles 19 of the prior art defibrillator 11 shown in FIGS. 1 and 2.

Figure 3:
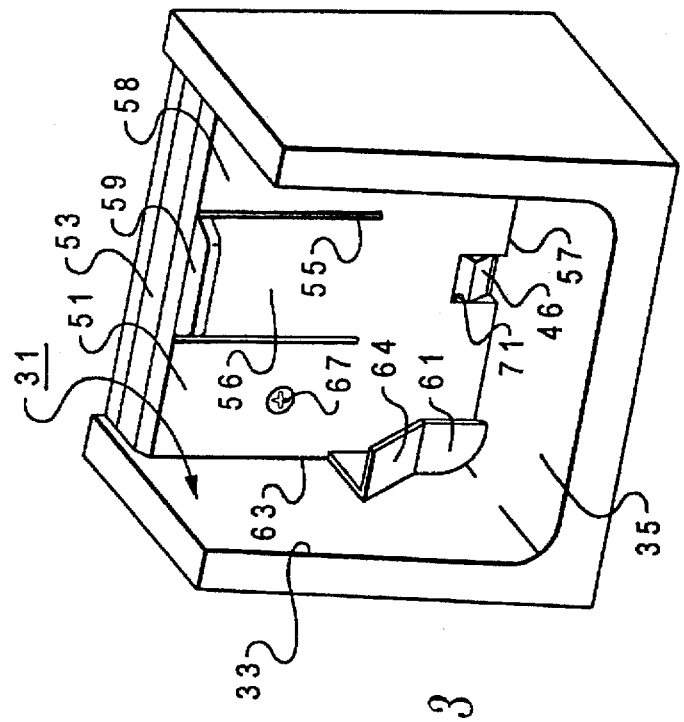
FIG. 3 is a perspective view of a defibrillator paddle retainer assembly of the preferred embodiment of the invention.
Figure 4:
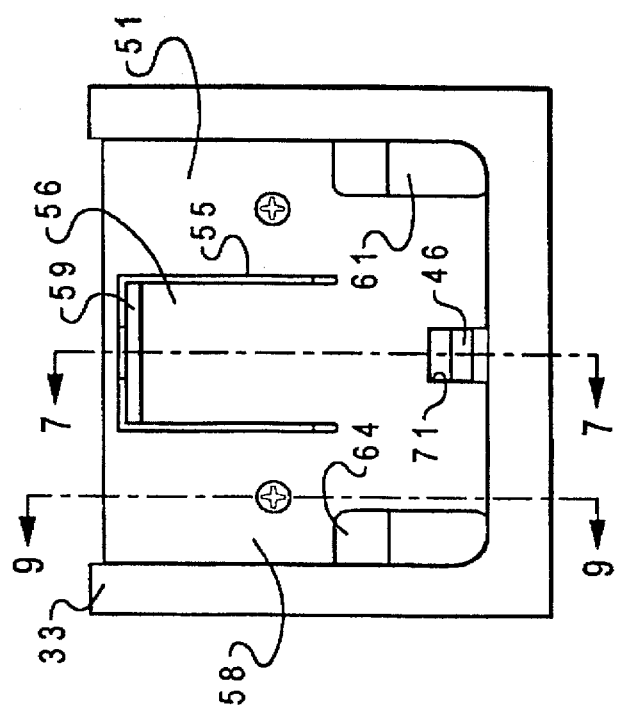
FIG. 4 is a front elevational view of the retainer assembly of FIG. 3.
Figure 5:
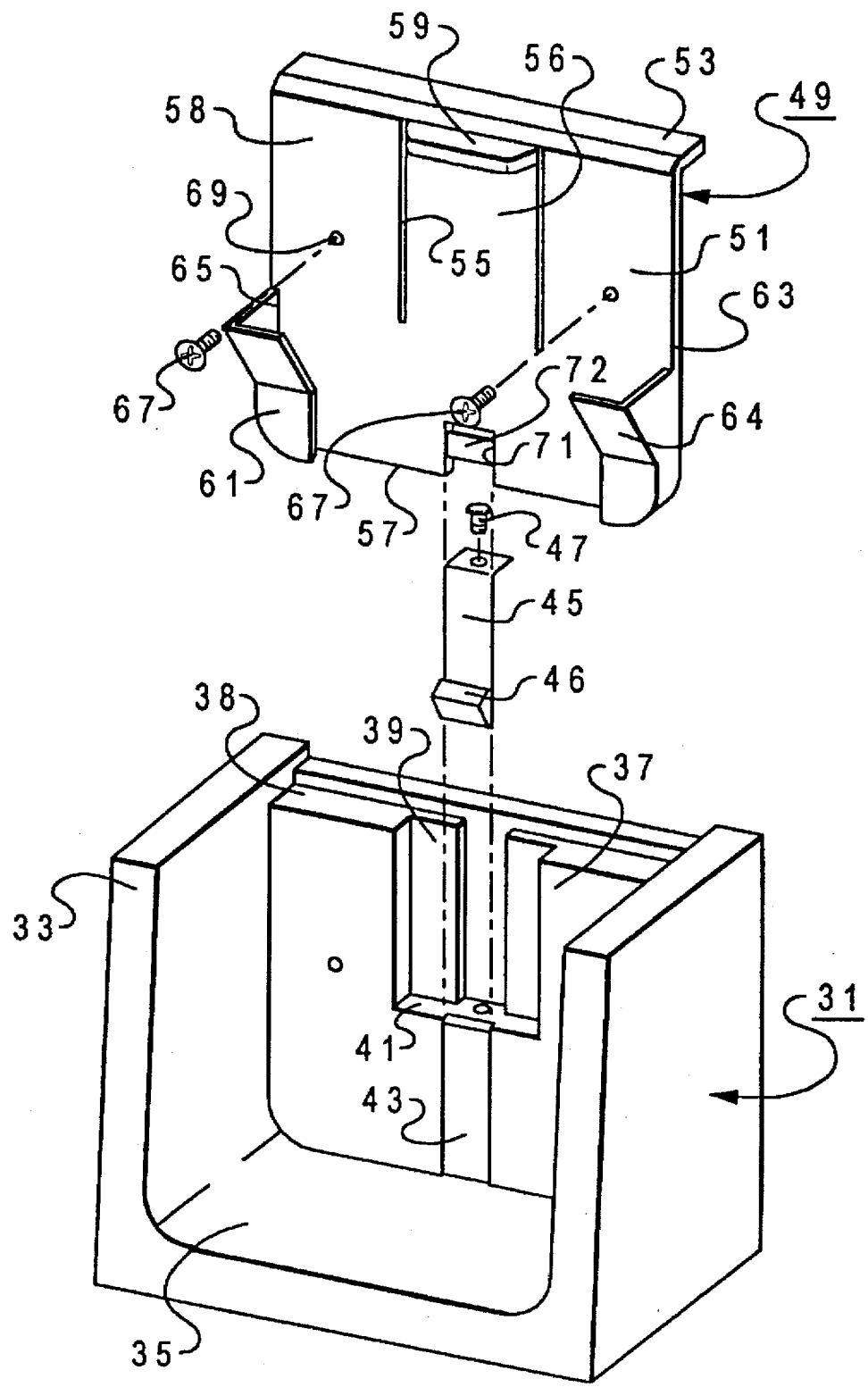
FIG. 5 is an exploded perspective view of the retainer assembly of FIG. 3.

Referring to FIGS. 3–5, pocket 31 is a cavity that has a pair of lateral, parallel opposed walls 33. Walls 33 extend in an outward direction from inner wall 35. Referring to FIG. 5, pocket 31 has a back wall 37 that is perpendicular to inner wall 35 and also to the lateral walls 33. Back wall 37 has an outer ledge 38 and a central recess 39. Recess 39 extends from outer ledge 38 toward inner wall 35, terminating in a ledge 41 about one-half the distance to inner wall 35.

An electrical strip slot 43, also centrally located, extends from recess ledge 41 to inner wall 35. Recess 39 and electrical strip slot 43 are rectangular. Recess 39 has a greater width than electrical strip slot 43, and the depth of recess 39 is greater than the depth of electrical strip slot 43. An electrical strip 45, which is a flat, resilient, conductive metal strip, locates in electrical strip slot 43. Electrical strip 45 has an outer end that is bent at 90° to overlie ledge 41, where it is secured by screw 47. The inner portion of electrical contact slot 43 has an electrical contact 46 in the shape of a clip. An electrical wire, not shown, is attached to screw 47 for electrically testing paddle 19 when it is located in pocket 31.

Referring still to FIG. 5, a retainer back plate 51 mounts to back wall 37. Back plate 51 has dimensions substantially the same as back wall 37. Back plate 51 has an outer flange 53 on its outer edge which is at an 90° angle relative to the remaining portion of back plate 51. Outer flange 53 overlies back wall outer ledge 38. A pair of parallel slits 55 extend from outer flange 53 toward inner wall 35. Slits 55 are laterally spaced apart so as to divide the outer portion of back plate 51 into approximately equal thirds from one lateral edge 63 to the other lateral edge of back plate 51. Slits 55 are perpendicular to outer flange 53 and extend approximately half the distance toward inner edge 57 of back plate 51. This defines a tab 56 between slits 55 and stationary side portions 58 on each lateral side of tab 56.

Figure 8:
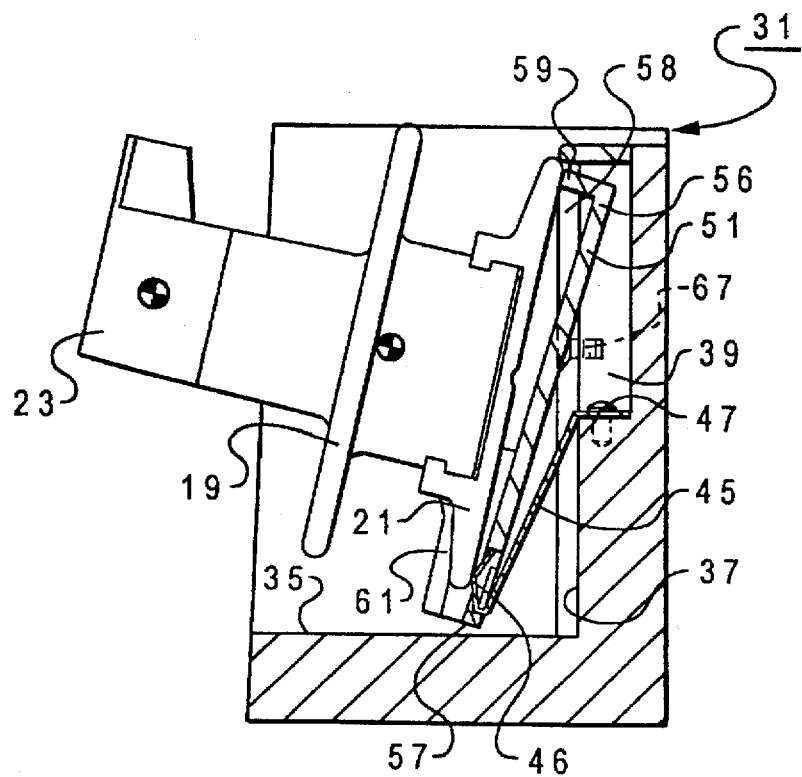
FIG. 8 is a sectional view similar to FIG. 7 of the retainer assembly of FIG. 3, but showing the defibrillator paddle in the process of being removed.

Back plate 51 is of a resilient flexible material such as a plastic, which enables tab 56 to flex in a rearward direction relative to side portions 58. A lip 59 locates at the outer edge of tab 56, extending the full width of tab 56. Lip 59 extends in a forward direction a short distance. Tab 56 has a width that is substantially the same as the width of recess 39 in back wall 37 so that tab 56 can flex rearward into recess 39, as illustrated in FIG. 8. When tab 56 is deflected in a rearward direction sufficiently, lip 59 will recess to a position substantially flush with side portions 58.

Figure 7:
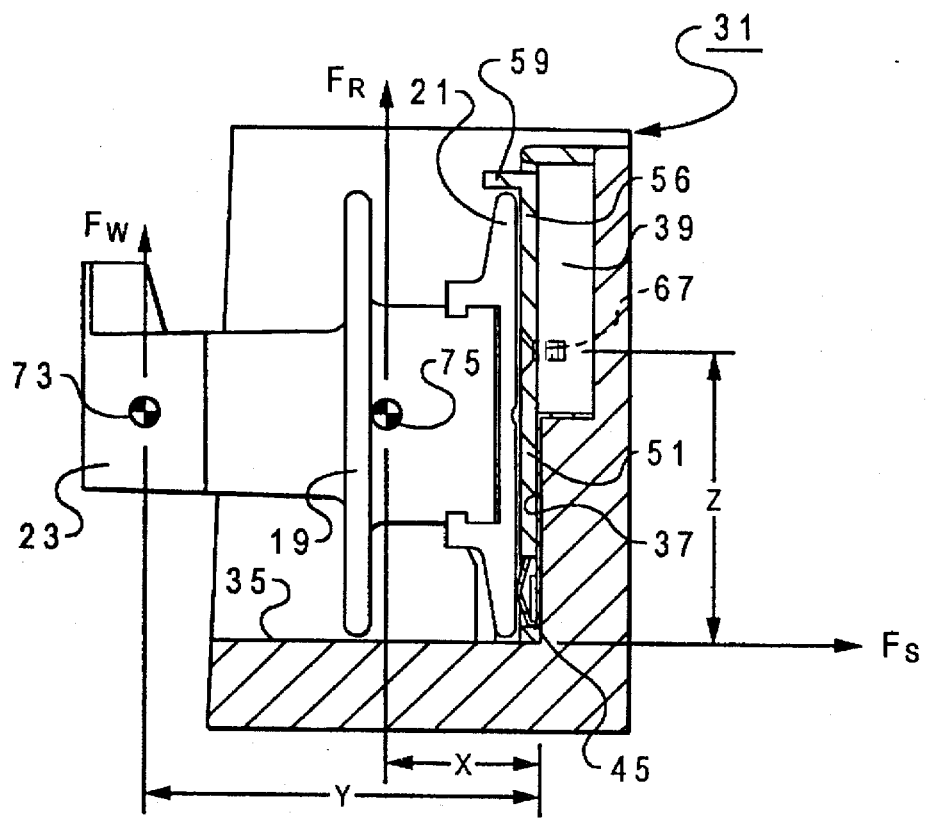
FIG. 7 is a sectional view of the retainer assembly of FIG. 3 taken along the line 7—7 of FIG. 4 and shown with a defibrillator paddle in the storage position.

A pair of braces or brackets 61 are integrally formed with back plate 51, each bracket 61 being located at each side edge 63 and extending forward a short distance from back plate 51. Each bracket 61 extends from inner edge 57 toward outer ledge 53 a distance that is somewhat less than one-half the total distance from inner edge 57 to outer ledge 53. Each bracket 61 extends forward from back plate 51 and has a guide portion 64 on its outer end that inclines forward at a 45 degree angle. Bracket 61 provides a slot for receiving an inner portion of the base 21 of paddle 19 as shown in FIG. 7. Each bracket 61 has a supporting portion at inner edge 57 that provides support for paddle base 21.

Figure 9:
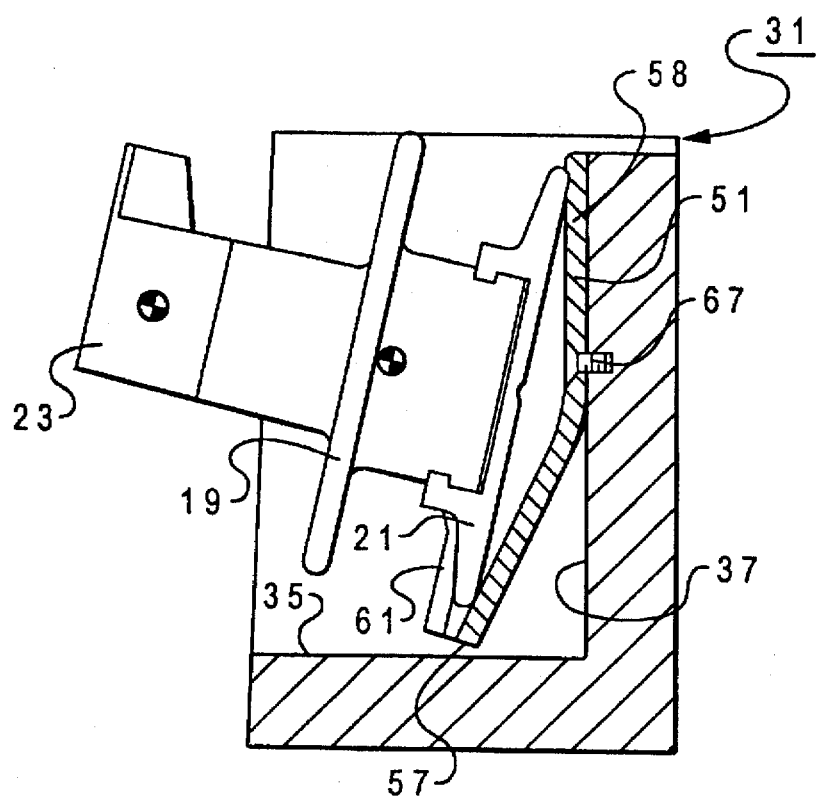
FIG. 9 is a sectional view of the retainer assembly of FIG. 3 taken along the line 9—9 of FIG. 4 and shown with a defibrillator paddle in the process of being removed.

Back plate 51 is pivotally mounted to back wall 37 by a pair of fasteners 67, which are shown to be screws. Fasteners 67 extend through holes 69 in back plate 51 into back wall 37. Holes 69 are located in the side portions 58 approximately in a midsection between inner edge 57 and outer ledge 53, but slightly closer to outer ledge 53 than inner edge 57. The inner portion of back plate 51, which is the portion extending from inner edge 57 to approximately the base of each slit 55, is completely free of any attachment to back wall 37 so that it will deflect in a forward direction as shown in FIG. 8. The outer portion of back plate 51, which extends from outer ledge 53 to approximately the bases of slits 55, is fastened to back wall 37 only by the fasteners 67. The fasteners 67 cause the side portions 58 to remain in stationary contact with back wall 37. A pivot point for the inner portion of back plate 51 is approximately at the midpoint of back plate 51, slightly below fasteners 67. The pivot point is not a precise single point, but comprises a gradual curved radius when the inner portion of back plate 51 bends relative to the side portions 58 as shown in FIG. 9.

To assemble the pocket 31, electrical strip 45 is secured in electrical strip slot 43 by screw 47. Back plate 51 is placed in contact with back wall 37 and secured by screws 67. The electrical contact 46 of electrical strip 45 will slide over a small tab or brace 72 provided in an aperture 71 at inner edge 57 of back plate 51. Brace 72 causes electrical contact 46 to remain stationary relative to aperture 71 when back plate 51 is deflected.

Figure 6:
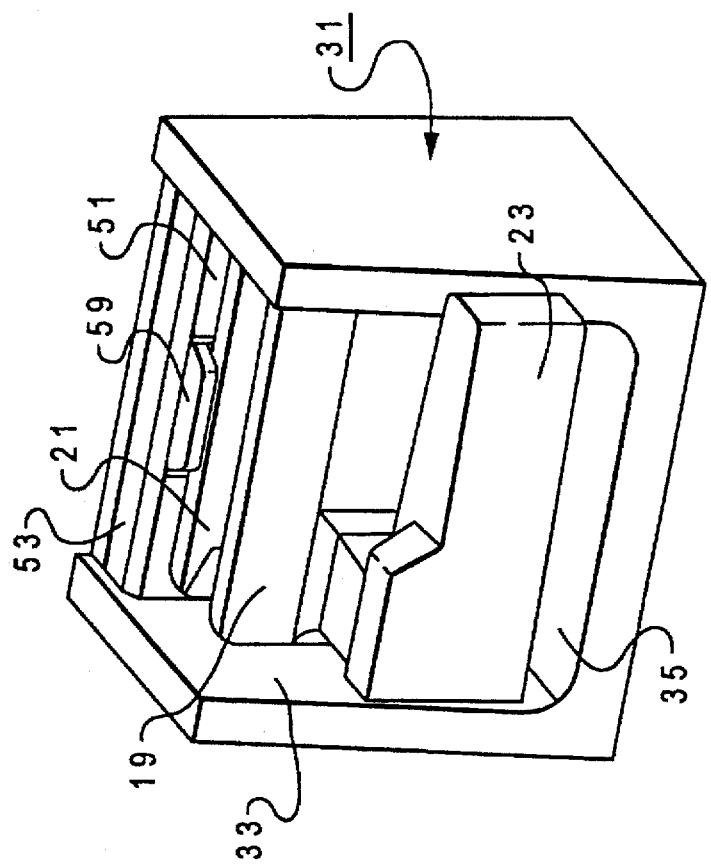
FIG. 6 is a perspective view of the retainer assembly of FIG. 3 and showing a defibrillator paddle located therein.

In use, paddle 19 is placed in pocket 31 by orienting the base 21 generally parallel to back plate 51 and sliding it inward. The inner portion of base 21 will slide into the slot formed by brackets 61. While sliding inward, back plate 51 will deflect about the pivot point, and the lip 59 will move into recess 39. Once paddle 19 has moved into its storage position, as shown in FIG. 6, lip 59 will snap forward and overlie an outer edge of base 21. The electrical contact 46 will frictionally engage the conductive base 21 of paddle 19. This allows the paddle 19 to be electrically tested while in pocket 31 by supplying test voltage to metal strip 45.

As shown in FIG. 7, paddle 19 is securely retained from outward movement by lip 59 and the resiliency of back plate 51. Electrical contact 46 exerts very little friction force for retaining paddle 19 in the slot. The handle 23 protrudes in a forward direction out of pocket 31. An axis of paddle 19 extends perpendicular to base 21 in a forward direction through handle 23. Numeral 73 indicates the centerline of the handle 23, while the numeral 75 indicates the center of mass of the paddle 19. Dimension X is the distance from the center of mass 75 to back wall 37. The dimension Y is the distance from the handle centerline 73 to back wall 37. The distance Z is the distance from the pivot point to the inner edge 57 of back plate 51. The symbol $F_S$ indicates the force of resiliency of the back plate 51, tending to resist the deflection illustrated in FIG. 8. $F_S$ acts in a rearward direction. $F_R$ is the retention force tending to dislodge the paddle 19 from pocket 31 by impact on the defibrillator housing 30 (FIG. 10), and it acts through the center of mass 75. The withdrawal force $F_W$, which also acts in the outward direction, acts through the handle centerline 73. The basic equations are as follows:

$$F_R \times X = F_S \times Z \text{ for paddle retention}$$
$$F_W \times Y = F_S \times Z \text{ for paddle withdrawal}$$
$$F_R \times X = F_W \times Y$$
$$F_R = F_W \times Y/X$$

Since Y is larger than X, the retention force $F_R$ is larger than the withdrawal force $F_W$. This differs from the prior art shown in FIG. 1 and 2 wherein the retention force generally equals the withdrawal force.

To remove paddles 19 from pockets 31 of defibrillator housing 30 (FIG. 10), the user grasps both handles 23, one in each hand, and pulls outward in unison as indicated by $F_W$. Because of lip 59, the pivotal mounting of back plate 51, and the moment exerted by $F_W$ times Y, this pull causes pivotal rotation of back plate 51 about the pivot point, as shown in FIGS. 8 and 9. The inner portion of paddle base 21 exerts a forward force on brackets 61, pushing the inner edge 57 of back plate 51 forward from back wall 37. Tab 56, not being restrained by back wall 37, deflects inward into recess 39. Tab 56 remains substantially in the same plane with the inner portion of back plate 51. The side portions 58 above fasteners 67 remain stationary because they are in overlying stationary contact with the outer portion of back wall 37 on each side of recess 39. The inner portion of back plate 51 from inner edge 57 to fasteners 67 curves at fasteners 67 and deflects forward as shown in FIG. 9. The deflection of tab 56 causes lip 59 to recess to a point wherein its forward edge is flush with side portions 58. This removes lip 59 from its overlying contact with the outer edge of base 21, allowing paddle 19 to be freely removed. During removal, the electrical contact 46 moves forward with the back plate inner edge 57 and metal strip 45 flexes, moving forward from electrical contact slot 43.

In addition to defibrillator paddles, retainer assemblies as described may be used for retaining other types of tools, such as cordless screwdrivers, drills, and the like.

We claim:

1. A retainer assembly for retaining a tool which has a handle and a center of mass, comprising:

retention means on said retainer assembly for slidingly receiving said tool to retain said tool with said retainer assembly against outward movement relative to said retainer assembly with a retention force of selected magnitude acting through said center of mass;

said retention means having a movable retainer member which has a storage position for engaging said tool to prevent outward movement of said tool, said retainer member being movable arcuately about a pivot point from said storage position to a release position, freeing said tool to be withdrawn from said retainer assembly, said retainer member being biased to the storage position; and wherein while retained by said retainer assembly, a withdrawal moment arm exists between said handle and said pivot point, and a retention moment arm of lesser length than said withdrawal moment arm exists between said center of mass and said pivot point, such that an outwardly directed pull on said handle with a withdrawal force of lesser magnitude than said retention force will move said retainer member from the storage position to the release position, allowing withdrawal of said tool from said retainer assembly.

2. The retainer assembly of claim 1 wherein said retention means comprises:

a back plate having an inner portion, an outer portion, and a forward side, said back plate being mounted to said retainer assembly at said pivot point, which is located at a junction of said inner portion and said outer portion, and being resilient to allow pivotal movement of said inner and outer portions about said pivot point;

bracket means on said forward side defining a slot for slidingly receiving an inner portion of said tool; and wherein said retainer member comprises:

lip means located on an outer portion of said back plate and extending forward from said back plate for overlying an outer portion of said tool when said tool is located in said slot.

3. A retainer assembly for retaining a tool which has a handle, comprising:

retention means on said retainer assembly for slidingly receiving said tool to retain said tool with said retainer assembly against outward movement relative to said retainer assembly with a retention force of selected magnitude;

said retention means having a release means actuable by an outwardly directed pull on said handle with a withdrawal force of lesser magnitude than said retention force for allowing withdrawal of said tool from said retainer assembly; wherein said retention means comprises:

a back plate having an inner portion, an outer portion, and a forward side;

bracket means on said forward side defining a slot for slidingly receiving an inner portion of said tool; and lip means located on an outer portion of said back plate and extending forward from said back plate for overlying an outer portion of said tool when said tool is located in said slot; wherein said back plate is flexible and resilient;

said retainer assembly has a back wall having a recess; and said release means comprises:

means for pivotally mounting said back plate to said back wall of said retainer assembly with said lip means adjacent to said recess such that an outward pull of sufficient force on said handle exerts a forward force on said bracket means, deflecting said inner portion of said back plate forward relative to said back wall and deflecting said lip means rearward relative to said back wall into said recess, away from contact with said outer portion of said tool to allow removal of said tool.

4. A retainer assembly for retaining a defibrillator paddle on a defibrillator housing, said paddle having a base on one end and a handle on an opposite end, comprising:

retention means on said retainer assembly for slidingly receiving said base of said paddle to retain said paddle on said housing in a storage position and to provide a retention force of selected magnitude against movement of said paddle in an outward direction relative to said retainer assembly; and said retention means having a release means actuable by an outwardly directed pull on said handle with a withdrawal force of lesser magnitude than said retention force for allowing withdrawal of said paddle from said retainer assembly.

5. The retainer assembly of claim 4 wherein said retention means comprises:

a back plate having an inner portion, an outer portion, and a forward side;

bracket means on said forward side defining a slot for slidingly receiving an inner portion of said base; and lip means located on an outer portion of said back plate and extending forward from said back plate for overlying an outer portion of said base when said base is located in said slot.

6. The retainer assembly of claim 5, wherein:

said back plate is flexible and resilient;

said retainer assembly has a back wall having a recess; and said release means comprises:

means for pivotally mounting said back plate to said back wall of said retainer assembly with said lip means adjacent to said recess such that an outward pull of sufficient force on said handle exerts a forward force on said bracket means, deflecting said inner portion of said back plate forward relative to said back wall and deflecting said lip means rearward relative to said back wall into said recess, away from contact with said outer portion of said base to allow removal of said paddle.

7. A retainer assembly for retaining a defibrillator paddle which has a base on one end which has inner and outer edges and a handle on an opposite end, comprising:

a pocket having a back wall which has a recess;

a resilient back plate having an inner portion and an outer portion;

a bracket secured to and extending forward from an inner portion of said back plate, defining a slot for slidingly receiving said inner edge of said base of said paddle;

a lip located on an outer portion of said back plate and extending forward from said back plate for overlying said outer edge of said base of said paddle when said paddle is located in said slot; and said back plate being pivotally mounted to said back wall with a part of said outer portion of said back plate which contains said lip being adjacent to said recess such that an outward pull of sufficient force on said handle exerts a forward force on said bracket, deflecting said inner portion of said back plate forward relative to said back wall and deflecting said lip rearward relative to said back wall into said recess, away from contact with said outer edge of said paddle to allow removal of said paddle.

8. The retainer assembly according to claim 7 wherein:

said outer portion of said back plate has a pair of parallel slits extending perpendicular to said lip, defining a central tab separating two stationary side portions; and said tab extends rearward into said recess when said lip is deflected in said rearward direction relative to said back wall while said side portions remain stationary.

9. The retainer assembly according to claim 8, wherein:

said side portions overlie an outer portion of said back wall; and said back plate is pivotally mounted to said back wall by at least one fastener which extends through at least one of said side portions into said outer portion of said back wall.

10. The retainer assembly according to claim 7, further comprising:

an electrical contact located in said slot for frictionally engaging said base of said paddle.

11. The retainer assembly according to claim 7, wherein there are two of said brackets spaced apart from each other at opposite lateral edges of said back plate.

12. A retainer assembly for retaining a defibrillator paddle which has a handle on one end and a base on an opposite end, comprising:

a pocket having an inner wall and a back wall extending substantially perpendicular to said inner wall;

a central recess formed in an outer portion of said back wall;

a resilient back plate having inner and outer edges and a pair of parallel slits extending from said outer edge partially toward said inner edge, defining a central tab and two side portions;

a bracket extending forward from said back plate adjacent said inner edge, defining a slot for slidingly receiving an inner edge of said base of said paddle;

a lip extending forward from said tab at said outer edge of said back plate for overlying an outer edge of said base of said paddle to retain said paddle in said slot with said base parallel to said back wall and with said handle extending forward relative to said back wall; and said back plate being mounted in abutment with said back wall by at least one fastener extending through one of said side portions of said back plate into said back wall at a sufficient distance from said inner edge of said back plate to create a pivot point, so that an outward pull of sufficient force on said handle exerts a forward force on said bracket, pivoting said inner edge of said back plate forward relative to said back wall, and said tab and lip rearward into said recess to allow removal of said paddle.

13. The retainer assembly according to claim 12 further comprising:

a electrical contact facing in a forward direction from said back plate in said slot for frictionally engaging said base of said paddle; and a flexible conductive member extending from said electrical contact to said back wall for electrically testing said paddle while said paddle is located in said pocket.

14. The retainer assembly according to claim 12 wherein said said fastener secures said one of said side portions of said back plate stationarily to said back wall so as to remain stationary relative to said back wall as said paddle is being withdrawn from said pocket.

15. The retainer assembly according to claim 12, wherein said back plate comprises two of said brackets spaced apart from each other at opposite edges of said back plate.

16. A defibrillator, comprising in combination:

a housing having at least one pocket which has a back wall;

at least one defibrillator paddle having a base on one end and a handle on an opposite end;

a retainer assembly in said pocket for retaining said paddle;

a resilient back plate having an inner portion and an outer portion;

a bracket secured to and extending forward from an inner portion of said back plate, defining a slot for slidingly receiving an inner edge of said base of said paddle;

a lip located on an outer portion of said back plate and extending forward from said back plate for overlying an outer edge of said base of said paddle when said paddle is located in said slot; and said back plate being pivotally mounted to said back wall such that an outward pull of sufficient force on said handle exerts a forward force on said bracket, deflecting said inner portion of said back plate forward relative to said back wall and deflecting said lip rearward relative to said back wall, away from contact with said outer edge of said paddle to allow removal of said paddle.

17. A method for retaining on and removing from a defibrillator a defibrillator paddle which has a base on one end and a handle on an opposite end, said defibrillator having a housing with a pocket which has a back wall, a resilient back plate mounted to said back wall, said back plate having a bracket secured thereto and extending forward from an inner portion of said back plate, defining a slot, and a lip located on an outer portion of said back plate extending forward from said back plate, said back plate being mounted to said back wall in a manner so as to allow said inner portion of said back plate to deflect forward and said lip rearward about a pivot point, the method comprising:

sliding an inner edge of said base of said paddle into said slot, forcing said lip to deflect rearward as said base slides past said lip, then resiliently snap forward to retain an outer edge of said base when said base is in said slot; then, to withdraw said paddle, exerting an outward pull on said handle, resiliently deflecting said inner portion of said back plate forward relative to said back wall and resiliently deflecting said lip rearward relative to said back wall about said pivot point, away from contact with said outer edge of said paddle to allow removal of said paddle.

* * * * *